(12) United States Patent
Kumar et al.

(10) Patent No.: US 6,704,587 B1
(45) Date of Patent: Mar. 9, 2004

(54) DUAL FUNCTION ASSAY DEVICE

(75) Inventors: Krishna S. Kumar, Duluth, GA (US); John J. Pasqua, Colfax, IN (US)

(73) Assignees: SpectRx, Inc., Norcross, GA (US); Altea Therapeutics Corp., Tucker, GA (US)

( * ) Notice: Subject to any disclaimer, the term of this patent is extended or adjusted under 35 U.S.C. 154(b) by 0 days.

(21) Appl. No.: 09/937,865

(22) PCT Filed: Mar. 31, 2000

(86) PCT No.: PCT/US00/08530

§ 371 (c)(1),
(2), (4) Date: May 21, 2002

(87) PCT Pub. No.: WO00/59371

PCT Pub. Date: Oct. 12, 2000

Related U.S. Application Data

(60) Provisional application No. 60/127,442, filed on Apr. 1, 1999.

(51) Int. Cl.[7] .................................................. A61B 5/00
(52) U.S. Cl. ........................ 600/316; 600/309; 600/347
(58) Field of Search .................................. 600/309–310, 600/316, 322, 347, 473, 476

(56) References Cited

U.S. PATENT DOCUMENTS

| | | | | |
|---|---|---|---|---|
| 5,348,003 A | * | 9/1994 | Caro ........................... | 600/310 |
| 5,423,803 A | * | 6/1995 | Tankovich et al. ............. | 606/9 |
| 5,458,140 A | * | 10/1995 | Eppstein et al. ............ | 600/573 |
| 5,899,856 A | * | 5/1999 | Schoendorfer et al. ..... | 600/362 |
| 6,077,660 A | * | 6/2000 | Wong et al. .................. | 435/4 |
| 6,479,015 B1 | * | 11/2002 | Long et al. ................. | 600/309 |

* cited by examiner

*Primary Examiner*—Max F. Hindenburg
*Assistant Examiner*—Matthew Kremer
(74) *Attorney, Agent, or Firm*—Needle & Rosenberg, P.C.

(57) ABSTRACT

A system and method for detecting substances such as glucose in tissue. The system comprises an assay device and an optical apparatus. The assay device comprises a reactive region that is responsive to at least one substance in fluid to be collected from the tissue when the fluid is in contact with the reactive region, and which reactive region is also responsive to a first type of optical energy suitable to heat up and transfer heat by conduction to the tissue to ablate the tissue and form at least one opening in the tissue from which fluid is collected. The optical apparatus has an activation head to which the assay device is attached, and a first optical energy source that outputs a first type of optical energy. An optical detecting device is included in the optical apparatus that measures a characteristic of the at least one substance from the response of the reactive region when the reactive region is in contact with the at least one substance.

27 Claims, 4 Drawing Sheets

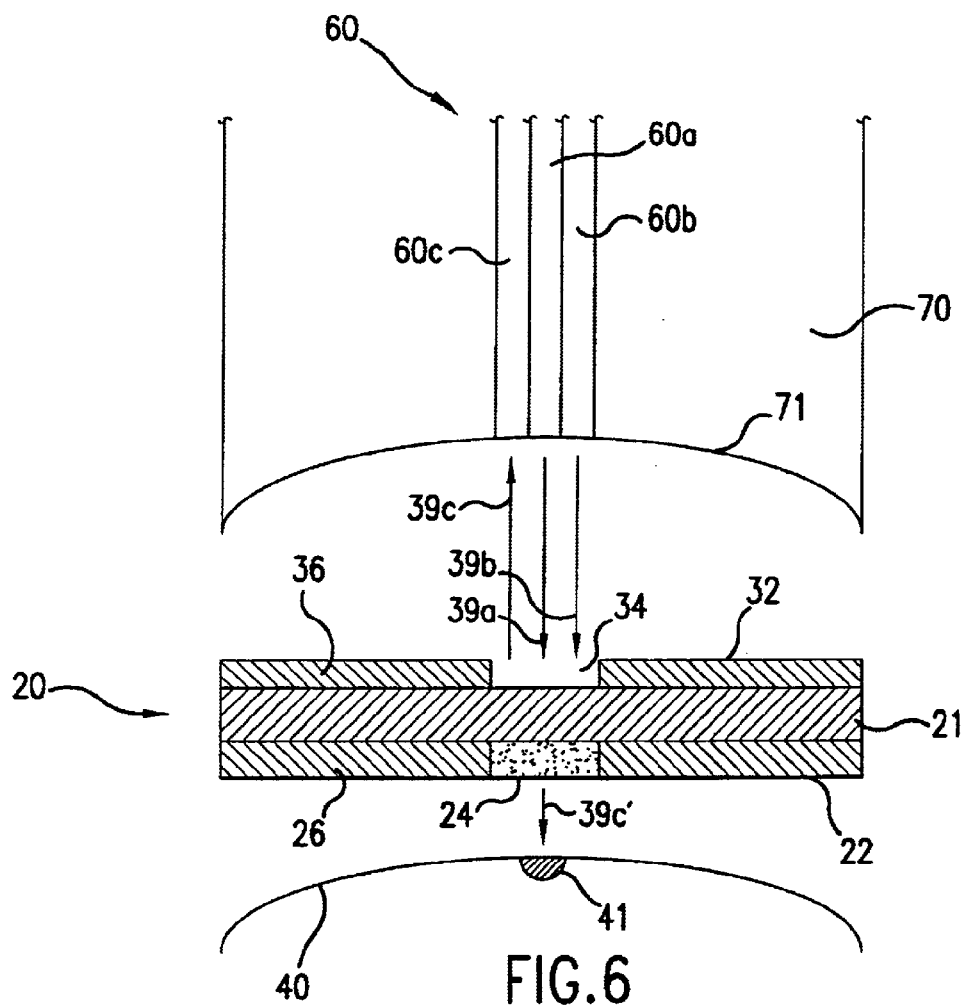
FIG.6
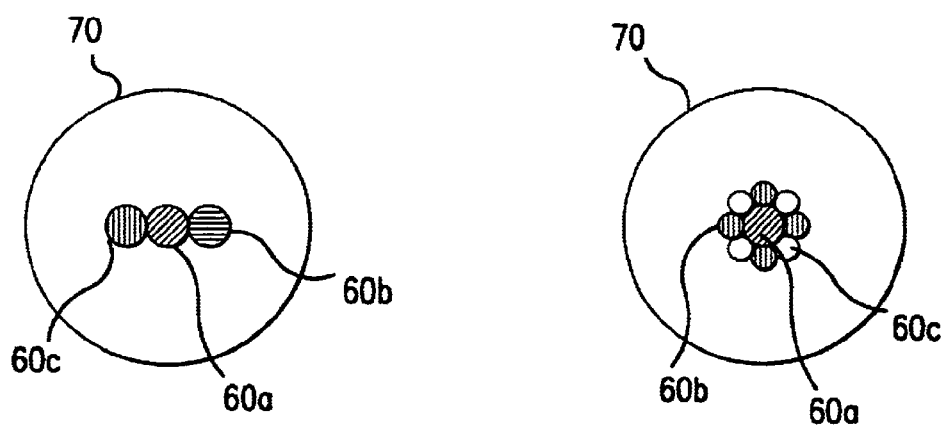
FIG.7
FIG.8

DUAL FUNCTION ASSAY DEVICE

The present application is a 35 U.S.C. §371 national phase application from, and claims priority to, international application PCT/US00/08530, filed Mar. 31, 2000 (published under PCT Article 21(2) in English), which claims priority to U.S. provisional patent application Serial No. 60/127,442, filed Apr. 1, 1999, which applications are hereby incorporated herein in their entirety.

This application claims the benefit of U.S. Provisional Application No. 60/127,442, filed Apr. 1, 1999, and entitled "Glucose Assay Method and Device," the entirety of which is incorporated herein by reference.

BACKGROUND OF THE INVENTION

1. Field of the Invention

This invention relates to an apparatus and method for detecting substances including glucose in a fluid to be collected from tissue.

2. Discussion of the Art

Glucose is an important substance for biological activities. For example, in individuals who may be affected by diabetes, there is a need to detect or measure the presence and amount of glucose as part of a daily routine. However, currently available measurement techniques often involve invasive testing. One method of glucose testing includes blood based assay testing. The "finger stick" blood assay testing technique currently is one widely accepted methodology for glucose testing results in the United States. Of course, this invasive approach requires that the drawing of blood to perform the test. This is quite uncomfortable to patients, especially to young patients. Moreover, this approach is time consuming.

Therefore, it is desirable to provide non-invasive or minimally-invasive techniques for measuring substances, such as glucose concentration, from fluids, such as blood and interstitial fluid.

SUMMARY OF THE INVENTION

Briefly, the present invention is directed to a system and method for detecting substances, such as glucose, in a fluid to be collected from a tissue. In one aspect, the system according to the present invention has an assay device and an optical apparatus. The assay device is suitable for attachment to the tissue, wherein the assay device is a dual function device that includes a reactive region that is responsive to at least one substance in fluid to be collected from the tissue when the fluid is in contact with the reactive region, and which reactive region is also responsive to a first type of optical energy suitable to heat up and transfer heat by conduction to the tissue to ablate the tissue and form at least one opening in the tissue from which fluid is collected. The optical apparatus has an activation head to which the assay device is attached, and a first optical energy source that outputs the first type of optical energy. An optical detecting device is included in the optical apparatus to measure a characteristic of the at least one substance from the response of the reactive region when the reactive region is in contact with the at least one substance in fluid.

In another aspect, the present invention provides a method for detecting a substance, such as glucose, in a fluid from a tissue. The method includes the steps of placing an assay on an activation head of an optical instrument, wherein the assay is responsive to at least one substance, positioning the activation head to the surface of the tissue so that the assay is in contact with the surface of the issue, forming at least one opening underneath the assay through the surface of the tissue, thereby to allow the fluid from the tissue to flow through the at least one opening and make contact with the assay, and detecting the response of the assay to the fluid to measure the presence of the at least one substance in the fluid. The method can be practiced by using the system in accordance with a preferred embodiment of the present invention.

According to yet another aspect of the present invention, an assay device is provided that includes a base having a first side and a second side, and a reactive region disposed or deposited on the first side of the base. The reactive region comprises a photosensitizing material that is placed in contact with the surface of the tissue and is responsive to a suitable electromagnetic energy emitted thereon so as to heat up and conductively transfer heat to the surface of the tissue to form at least one opening, thereby to allow fluid from the tissue through the at least one opening to contact with the assay. Moreover, the photosensitizing material is further responsive to at least one substance in the fluid, from which a characteristic of the at least one substance is detected based upon electromagnetic energy scattered and/or reflected therefrom.

Additional advantages and features of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed. These and other features and advantages of preferred forms of the present invention are described herein with reference to the drawing figures.

BRIEF DESCRIPTION OF THE DRAWINGS

FIG. 6 shows a cross-sectional, partial view of the assay device and activation head of the optical apparatus shown in FIG. 1 in operation.

FIG. 7 shows a cross-sectional, bottom view of a first embodiment of an activation head of the optical apparatus shown in FIG. 1 according to the present invention.

FIG. 8 shows a cross-sectional, bottom view of a second embodiment of an activation head of the optical apparatus shown in FIG. 1 according to the present invention.

Figure 1:
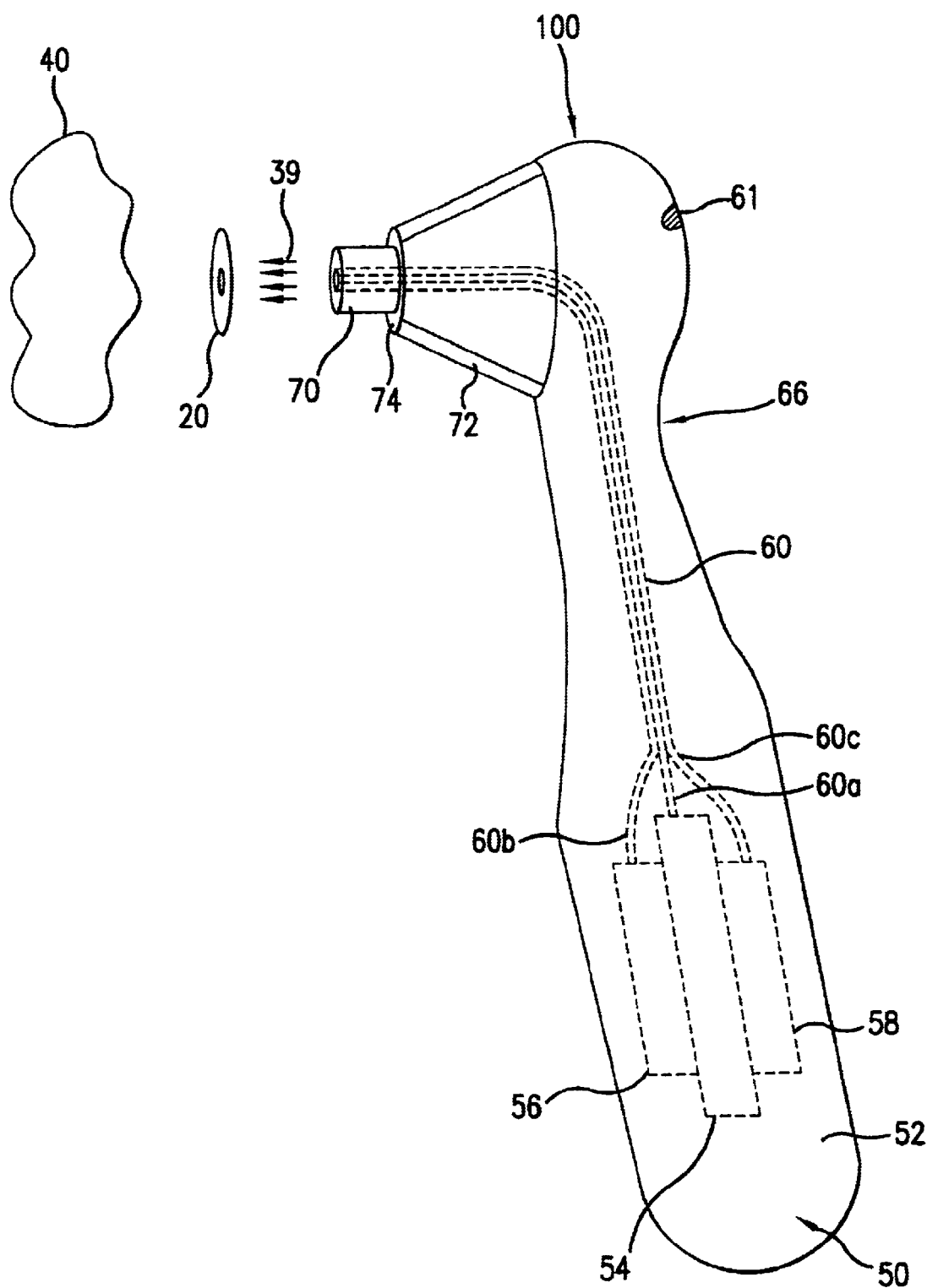
FIG. 1 is a schematic diagram of a system for detecting at least one substance in a fluid to be collected from a tissue according to the present invention.

DETAILED DESCRIPTION OF THE DRAWINGS
Definitions

As used herein, the term "biological fluid" or "fluid" at least includes "interstitial fluid" (ISF), which is the clear fluid that occupies the space between the cells in the body, or blood.

As used herein, the term "tissue" means an aggregate of cells of a particular kind, together with their intercellular substance, that form a structural material of an animal or plant. At least one surface of the tissue must be accessible to electromagnetic radiation so that the invention can be carried out. The preferred tissue is the skin. Other tissues suitable for use with this invention include mucosal tissue and soft organs.

As used herein, the term "glucose" means a monosaccharide also known as D-glucose, D-glucopyranose, grape sugar, corn sugar, dextrose, and cereiose. Glucose occurs in the animal body fluids, for example, in blood, lymphy, or interstitial fluid. Glucose enters the bloodstream by absorption from the small intestine. It is carried via the portal vein to the liver, where part is stored as glycogen, the remainder reentering the circulatory system. Another site of glycogen storage is muscle tissue.

As used herein, "analyte," "substance," or any such similar term means a component that is being detected or measured in an analysis. In particular, the analyte may be any chemical or biological material or compound suitable for passage through a biological membrane technology known in the art, of which an individual might want to know the concentration or activity inside the body. Glucose is a specific example of an analyte because it is a sugar suitable for passage through the skin. Individuals, for example those having diabetes, might want to know their blood glucose levels. Other examples of analytes include, but are not limited to, such compounds as sodium, potassium, billirubin, urea, ammonia, calcium, lead, iron, lithium, salicylates, pharmaceutical compounds, and the like.

As used herein, "poration," "microporation," or any such similar term means the formation of a small hole or pore or opening to a desired depth in or through the biological membrane, such as skin or mucous membrane, or the outer layer of an organism to lessen the barrier properties of this biological membrane to the passage of biological fluids, such as analytes from below the surface for analysis. Preferably the hole or micropore will be no larger than about 1 mm (1000 $\mu$m) in diameter, and will extend to a selected depth, as described hereinafter.

As used herein, "micropore" or "pore" means an opening formed by the microporation method.

As used herein, the term "reagent," "active component," or any other similar term means any chemical material or compound suitable for use by the methods previously known in the art and/or by the methods taught in the present invention, that induces a desired effect, such as a biological, or optical effect, or other observable effect, which may include but is not limited to (1) producing a detectable shift in this compound or formulation's measurable response to the application of energy to this area which may be electromagnetic, mechanical, thermal, optical or acoustic when in contact with at least one substance in a fluid to be collected from a tissue, (2) producing a response when in contact with at least one substance in a fluid to be collected from a tissue so as to allow a characteristic of the at least one substance can be measured or detected from the response; and/or (3) being responsive to a type of electromagnetic energy emitted thereon when in contact with a tissue to heat up and transfer heat by conduction to the issue to ablate the tissue and form at least one opening in the tissue from which a fluid can be collected. As used herein, the term "photosensitizing material" means a material that contains at least one reagent or active component, which at least is responsive to at least one substance in a fluid and to a type of electromagnetic energy emitted thereon when in contact with a tissue to heat up and transfer heat by conduction to the issue to ablate the tissue.

The present invention is directed to a system and method for detecting at least one substance in a fluid to be collected from a tissue. For example, the system and method are described in connection with an application for detecting glucose in interstitial fluid or blood collected from a human being. Obviously, the system and method according to the present invention can be used to detect other substance(s) in any biological fluids.

Specifically, FIG. 1 shows a system 100 which utilizes a disposable assay device 20 in combination with an optical apparatus 50 for detecting a substance such as glucose in a fluid to be collected from a tissue 40. The optical apparatus 50 includes a housing 52 that is approximately the size of a human hand. A first energy source 54, a second energy source 56, and a detecting instrument 58 are located inside housing 52. First energy source 54, second energy source 56, and detecting instrument 58 are coupled to an activation head 70 via optical fiber (s) 60. Activation head 70 is received in an open end 74 of a holder 72 of housing 52. Holder 72 can have any shape depending, among other things, on the shape of activation head 70 and hence may alternatively be referred to as an activation head receiving element. In a preferred embodiment as shown in FIG. 1, holder 72 is cone-shaped. Holder 72 can be a separate piece or part of housing 52. It is preferable that holder 72 be capable of receiving activation head 70, to allow a glucose measurement to be made by using a disposable assay device 20, but then allowing disposable assay device 20 to be readily removed after a measurement performed, and then allowing a new assay device 20 to be attached to the activation head 70 again so that system 100 is ready to perform a new measurement. The optical apparatus 50 shown in FIG. 1 is derived from an apparatus disclosed in commonly assigned U.S. Pat. No. 5,792,049, which is incorporated herein by reference.

In a preferred embodiment, first energy source 54 transmits a first type of energy in the form of electromagnetic radiation 39 with sufficient intensity. Preferably, the first energy source 54 is an optical energy source, such as a laser, that provides stimulated emission of radiation and operates in the infrared, visible, or ultraviolet region and is suitable for practicing the present invention. Alternatively, the first energy source 54 can be a laser diode, a radio signal generator, a microwave signal generator, an acoustic signal generator, a visible signal generator, an ultraviolet signal generator, an x-rays generator, a $\gamma$-rays generator, an $\alpha$-rays generator, a $\beta$-rays generator, or any other type of electromagnetic signal generator.

The second energy source 56 provides a second type of energy as output to a subject, i.e., the assay device 20. Preferably, the second energy source 56 is an optical energy source such as a light bulb, a tungsten halogen bulb, a noble gas filled tungsten bulb, one or several LEDs, or other similar optical devices covering the desired regions of a target optical spectrum. The second energy source 56 transmits the second type of energy to the activation head 70 through optical fiber(s) 60. The activation head 70 projects the second type of energy onto the assay device 20. Alternatively, the second energy source 56 can be placed at a location within housing 52 and near the holder portion 72 to output the second type of energy to the assay device 20 directly. For the embodiments where the second energy source 56 provides optical energy, the optical energy is output to the assay device 20 through the activation head 70 to illuminate the assay device 20, which is in contact with fluid from the tissue 40. Optical energy scattered and/or reflected from the assay device 20 can be collected and transmitted to the detecting instrument 58 through activation head 70 to detect and/or measure the presence of at least one substance in the fluid from the tissue 40, such as glucose. Note that although in the embodiment shown in FIG. 1, first and second energy sources 54, 56 are separate elements, it is also envisioned that a single energy source may provide both first and second types of energy. An example of such an energy source is a laser with an adjustable intensity and bandwidth. The optical apparatus 50 can include a control unit (not shown) to control application of the first type of energy from the first energy source 54, the second type of energy from the second energy source 56 and processing of energy received by the detecting instrument 58.

Still referring to FIG. 1, detecting instrument 58 is an optical detecting device, such as a spectrometer. The spectrometer can, for example, include a microspectrometer offered by American Laubscher Corporation of Farmingdale, N.Y., called the VIS/NIP microspectrometer. The detecting instrument 58 can be other kinds of electromagnetic signal detectors such as specified band detector(s). The detecting instrument 58 is coupled to the activation head 70 through one of the optical fibers 60 to detect and/or measure a characteristic of at least one substance such as glucose in a fluid collected from the tissue 40 based on energy spectrum corresponding to an interaction between the assay device 20 and the glucose in a fluid collected from the tissue 40. The energy spectrum includes electromagnetic energy scattered and/or reflected from the assay device 20 which is irradiated by at least one of the first energy source 54 and the second optical energy source 56. For the embodiment where the second energy source 56 is used to illuminate the assay device 20, the energy spectrum includes light within a waveband indicative of the substance, such as glucose, in the fluid scattered and/or reflected from the assay device 20, and the desirable optical interaction can include the appearance and/or change of color (visible or invisible) in a region of the assay device 20. Alternatively, the presence of a substance can be measured if the energy spectrum detected by the detecting instrument 58 does not have a component with a specific waveband otherwise indicative of the substance. Furthermore, depending on the types of first and second energy sources 54, 56 and/or the type of photosensitizing material used in the assay device 20 as discussed in more detail below, the presence of a substance in a fluid, such as glucose, can be measured using Fluorescence intensity, Fluorescence lifetime, surface plasmon resonance, Fluorescence polarization, circular dichroism, Raman scattering and other known technologies, or a combination of at least two of these technologies in conjunction with the embodiments of the present invention. The assay device 20 has a reactive region that is responsive to glucose and in contact with the fluid as discussed in more detail below. The detecting instrument 58 preferably has a sensor (not shown) responsive to energy reflected from and/or scattered by the assay device 20, and a processor (not shown) coupled to the sensor for receiving and processing an output of the sensor to determine the presence of the at least one of the substances. Further a display (LCD or other type) disposed on the exterior of the optical apparatus 50 may be coupled to the detecting instrument to display a measurement.

Optical fiber(s) 60 can be a single flexible transparent fiber device containing a bundle of optical fibers or a bundle of flexible transparent fiber devices. Preferably, optical fiber(s) 60 are light guides having fiber properties and requirements for image transfer, in which information is continuously transmitted over relatively short distances. Optical fiber(s) 60 can be any one, or a combination of multimode, stepped refractive index profile fibers, graded index multimode fiber, and a single-mode, stepped index fiber. Preferably, however, optical fiber(s) 60 is a single or combination of multimode, stepped refractive index profile fibers. For example, optical fibers made by 3M Corporation, having a diameter range of 1–1000 microns, can be used to practice the present invention.

In one embodiment of the present invention as shown in FIG. 7, optical fiber(s) 60 includes optical fibers 60*a*, 60*b*, and 60*c* for electromagnetic energy transmission for the first energy source 54, the second energy source 56 and the detecting instrument 58, respectively. In another embodiment of the present invention as shown in FIG. 8, optical fiber(s) 60 includes a bundle of several flexible transparent fiber devices 60*a*, 60*b*, and 60*c*. For example, optical fiber 60*a* couples the first energy source 54 to the activation head 70, optical fibers 60*b* couple the second energy source 56 to the activation head 70, and optical fibers 60*c* couple the detecting instrument 58 to the activation head 70. Note that as shown in FIG. 8, there are several optical fibers 60*b* and 60*c* to enhance the ability of the activation head 70 to output the second type of energy to, and collect energy scattered and/or reflected from, the assay device 20.

Referring back to FIG. 1, curved portion 66 of housing 52 allows a user's hand to comfortably hold and position system 100 which includes the optical apparatus 50 with attached assay device 20 so as to press the assay device 20 firmly against the tissue 40 to conduct a measurement. A person can initiate a measurement as the case may be, by pressing a push button 61 with his or her thumb.

The activation head 70 has a concavely-curved portion 71, as shown in FIG. 6. Note that FIG. 6 shows for explanatory purposes the activation head 70 being spaced from the tissue 40; in actual operation, the assay device 20 is attached to the activation head 70 and is in contact with the tissue 40. A concavely-shaped activation head 70 allows the assay device 20 closely in contact with the tissue 40 when the assay device 20 is pressed against the tissue 40 by the activation head 70. Moreover, the activation head 70 is preferably made of material suitable for absorbing heat from the tissue generated by the reactive region 24 during operation. The activation head 70 thus serves as a heat sink to reduce the sensation to the subject, such as a patient, by removing the heat from the tissue incidentally created during the operation process. The material of the activation head 70 is aluminum or other suitable metals or alloys that have good heat sinking characteristics.

Figure 2:
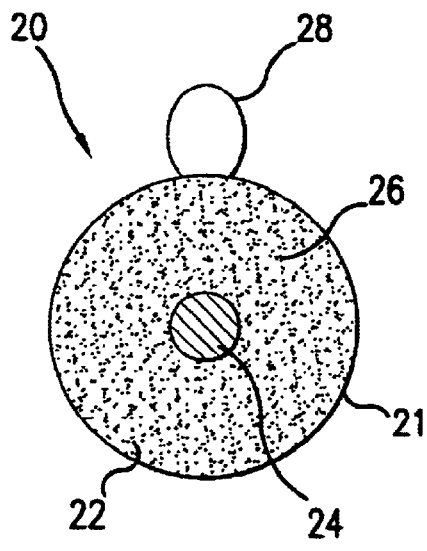
FIG. 2 shows a first side of an assay device in connection with the system shown in FIG. 1 according to the present invention.
Figure 3:
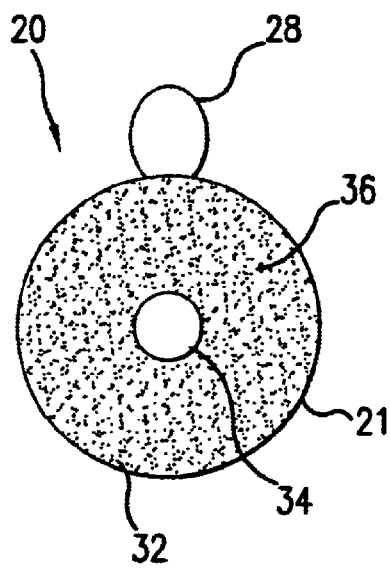
FIG. 3 shows a second side of an assay device in connection with the system shown in FIG. 1 according to the present invention.
Figure 4:
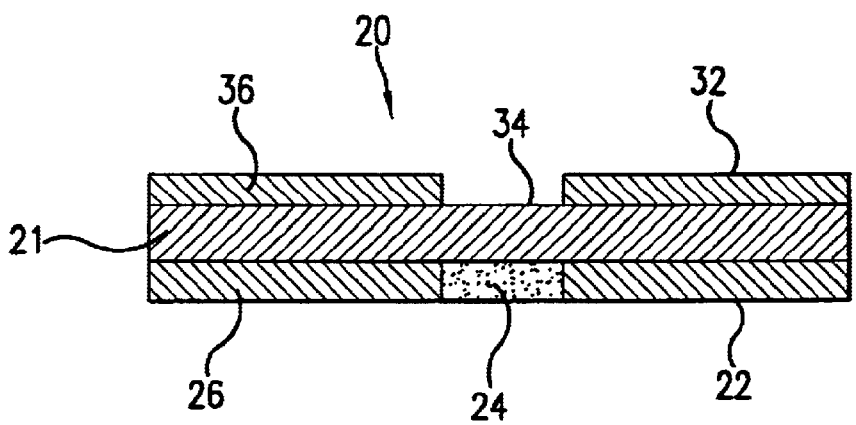
FIG. 4 shows a cross-sectional side view of an assay device in connection with the system shown in FIG. 1 according to the present invention.

Referring now to FIGS. 2–4 in conjunction with FIG. 6, according to a preferred embodiment of the present invention, the assay device 20 includes a base or support member 21 having a first side 22 and a second side 32. The base 21 can be a small disk-shaped member made from fiber or other suitable material(s) transparent to the first and second types of energy output by the first and second energy sources 54, 56. Alternatively, base 21 can be oval, square, triangular, or any other geometric shape. Likewise, base 21 can be made from plastics, polymers, thin film of metal, paperboards, or other types of materials. As shown in FIGS. 2, 4, and 6, the first side 22 of the assay device 20 has a reactive region 24 or a microdot disposed or deposited on the first side 22. Preferably, the reactive region 24 is substantially located at the center area of the first side 22. In a preferred embodiment of the present invention, the reactive region 24 includes a layer of photosensitizing material, which is responsive to the electromagnetic energy output by the first energy source 54 so as to heat up and conductively transfer heat to the surface of the tissue 40 to form at least one opening or micropore 41 as shown in FIG. 6, thereby to allow fluid from the tissue 40 through the at least one opening or micropore 41 to contact with the first side 22 of the assay device 20. This microporation technique is described in commonly assigned U.S. Pat. No. 5,885,211, which is incorporated herein by reference. Moreover, the reactive region 24 or the layer of photosensitizing material is responsive to a substance of interest in the fluid, to alter in a detectable manner electromagnetic energy scattered by and/or reflected from the reactive region 24 in response to application of the second type of optical energy thereby indicating a characteristic of the at least one of the substances in the tissue 40.

The first side 22 of the assay device 20 optionally has adhesive material 26 disposed or deposited thereon as to leave the reactive region 24 substantially uncovered, as shown in FIG. 2. The adhesive material 26 can be used to attach the assay device 20 to the tissue 40 when the activation head 70 presses the assay device 20 to the tissue 40. The assay device 20 optionally has adhesive material 36 deposited on the second side 32. The adhesive material 36 can be used to attach the assay device 20 to the activation head 70 of the optical apparatus 50. Optionally, the adhesive material 36 is disposed on the base 21 to form a mask around a window 34 opposite the reactive region 24 of the first side 22. The window 34 allows the output electromagnetic energy 39a from the first energy source 54, such as a laser, to reach and heat up the reactive region 24 of the first side 22, which then transfers heat 39c' to the surface of the tissue 40 to form at least one opening or a micropore 41 as shown in FIG. 6, thereby to allow fluid from the tissue through the at least one opening 41 to contact with the reactive region 24 of the first side 22. The window 34 also allows the output electromagnetic energy 39b from the second energy source 56 to reach the reactive region 24 and cause a desirable optical interaction with the reactive region 24 that can then be detected from scattered by and/or reflected energy 39c, as explained above.

Referring back to FIGS. 2 and 3, optionally, the assay device 20 has a tear tab 28. Tear tab 28 can be an integral part of the base 21, or a separate component attached to the base 21 by glue or other kind of adhesive material or heat sealing, etc. Tear tab 28 can be used to handle or transport the assay device 20, prior, during or after a measurement. For example, prior to a measurement to be performed, tear tab 28 can be used to attach the assay device 20 to the activation head 70 of the optical apparatus 50. Likewise, once a measurement has been performed, tear tab 28 can be used to peel the assay device 20 away from the activation head 70. A new assay device 20 can then be attached to the activation head 70 and system 100 is now ready to make another measurement on tissue 40.

The photosensitizing material used in the reactive region 24 preferably includes a formulation of active components and/or inactive components. As explained above, the formulation of the photosensitizing material provides at least two functions: one function to react with one or more substances of interest to allow for detection thereof by electromagnetic means; and a second function to absorb a certain type of electromagnetic energy focused thereon to heat up and conductively transfer heat to adjacent tissue and form at least one opening therein. In one embodiment of the present invention, the inactive components include a number of well-known polymeric binders that can both stabilize and hold the active components in place. These polymeric binders include, but are not limited to, polyvinylpyrrolidone, polyvinyl alcohol, polyethylene glycol, bovine serum albumin, and collagen. Optionally, a surfactant that will allow for more even spreading and quicker re-solubilization of the active components can be added as an inactive component. There are many choices for the surfactant suitable for the present invention, such as sodium dodecyl sulfate, Triton X-100, cholate, dioctylsulfosuccinate, polyoxyethylenesorbitans such as Tween 20 and Span 20, and polyoxyethylene ethers such as Brij 35, etc.

In another preferred embodiment of the present invention, a buffer can be included in the formulation as an inactive component. Commonly used buffers are citrate, phosphate and a variety of "biological buffers" such as HEPES, MES, Bis-Tris, BES, ADA, ACES, MOPSO, MOPS, Bis-Tris propane, TES, etc. The addition of a buffer to the formulation can improve the stability and performance of the photosensitizing material. However, the choice of the buffer system will greatly depend on the choice of an indicator system as discussed below.

The active components of the layer of photosensitizing material include an enzyme system and an indicator of the at least one of the substances in the tissue 40 to be measured. In a preferred embodiment of the present invention, the active components include specific enzymes or compounds with a high binding affinity for glucose and can include an auxiliary enzyme or mediator. These components are used in conjunction with one or more indicators such as chromogens or fluorescent probes to produce a change in the absorption or absorption and emission spectra, respectively.

One enzyme system that is useful in a preferred embodiment of the present invention is the glucose oxidaseperoxidase system. This enzyme system can be used in conjunction with a variety of indicators such as either 4-aminoantipyrine (4-AAP) or 3-methyl-2-benzothiazolone hydrazone (MBTH) with a variety of derivatives of phenol or aniline. These derivatives include phenol, p-hydroxybenzoic acid, p-hydroxybenzene sulfonate, aniline, N-ethyl-N-(2-hydroxy-3-sulfopropyl)-3,5-dimethyl aniline, N-ethyl-N-(2-hydroxy-3-sulfopropyl)-3-methyl aniline, N-ethyl-N-(2-hydroxy-3-sulfopropyl) aniline, N-(2-hydroxy-3-sulfopropyl) aniline, etc. Some indicator systems that can be used with the glucose oxidaseperoxidase system require just one chromogen and can be used without 4-AAP or MBTH. Examples of such indicators are ortho-dianisidine, ortho-toluidine, 3,3',5,5'-tetramethylbenzidine, ABTS and others.

Another enzyme system that is useful in a preferred embodiment of the present invention is glucose dehydrogenase and AND. This enzyme system can either be used as is with ultraviolet detection of NADH or coupled with either an electron mediator (or diaphorase) with a chromogen. The electron mediator can come form the class of compounds such as ferrocyanide, phenazine methosulfate or phenazine ethosulfate. The indicator can be one of the common tetrazolium dyes, such as iodo-nitrotetrazolium, neo-tetrazolium blue, nitro-tetrazolium blue or some of the newer water-soluble tetrazoliums (WSTs).

There exists a large class of stains (dyes and pigments) used for cytological staining that can be used with either the glucose oxidase/peroxidase system or the glucose dehydrogenase system to serve the function of absorbing electromagnetic (optical) energy of the first type to form openings in the tissue, as described above.

Moreover, to detect the presence of glucose, instead of using enzymes, glucose binding proteins can be used in a preferred embodiment of the present invention. Such glucose binding proteins are nondestructive and are based on a signal change upon glucose binding. The glucose detecting system that utilizes glucose binding proteins as active components is commonly fluorescence based. At least two types of glucose binding proteins can be used in the present invention. One is a single molecule system, and the other is a bimolecular or multimolecular system.

In a single molecule system, according to one embodiment of the present invention, the binding molecule has conjugated to it two fluorophores with the property that the emission spectrum of one of the fluorescent dyes (donor) overlaps with the absorption spectrum of the other dye (acceptor). Upon binding there is a usually a conformational change in the protein molecule that changes the relative distance between the two dyes. Typically, the dyes move closer to each other. Glucose binding proteins that are candidates for this type of work are Glucose-Galactose Binding Protein (GGBP), hexokinase (in the absence of ATP) and apo-glucose oxidase. Any of a large number of molecules that undergo conformational change upon glucose binding that can be used to practice the present invention. Upon irradiation with a wavelength that excites the donor dye, the proximity of the two dyes determines what percentage of the excited donor dyes will be nonradiatively transferred to the acceptor dye; the closer the two dyes, the more of this quantum energy transfer occurs. This process is called Fluorescence Resonance Energy Transfer (FRET). The amount of FRET measured is directly related to the glucose concentration. This nonradiative transfer can be measured in a number of ways: by measuring the intensities of the light emitted from the donor and acceptor dyes, by measuring the fluorescence lifetime of the donor dye, and/or by measuring the decrease in fluorescence polarization relative to the incident light.

According to another preferred embodiment of the present invention, in a bimolecular system, a macromolecule that includes a single or multiple glucose molecule(s) is conjugated with a donor or acceptor fluorescent dye. While a glucose binding protein is conjugated with the other dye, i.e., if the glucose bearing molecule is conjugated with a donor dye, then the glucose binding protein is conjugated with the acceptor dye. A common glucose binding protein used in this application is Concanavalin A. Other lectins and GGBP, hexokinase and apo-glucose oxidase can also be used to bind glucose in this system. Again, the amount of FRET that occurs in this bimolecular system is proportional to the glucose concentration and is measured in the same ways as in the monomolecular system described above.

The photosensitizing material is disposed or deposited onto the base 21 as a thin film, or as a microdot, as known to those skilled in the art, or as an aggregation of powders containing a formulation of inactive components and active components as described above. The reactive region 24 is formed and defined by the photosensitizing material.

Figure 5:
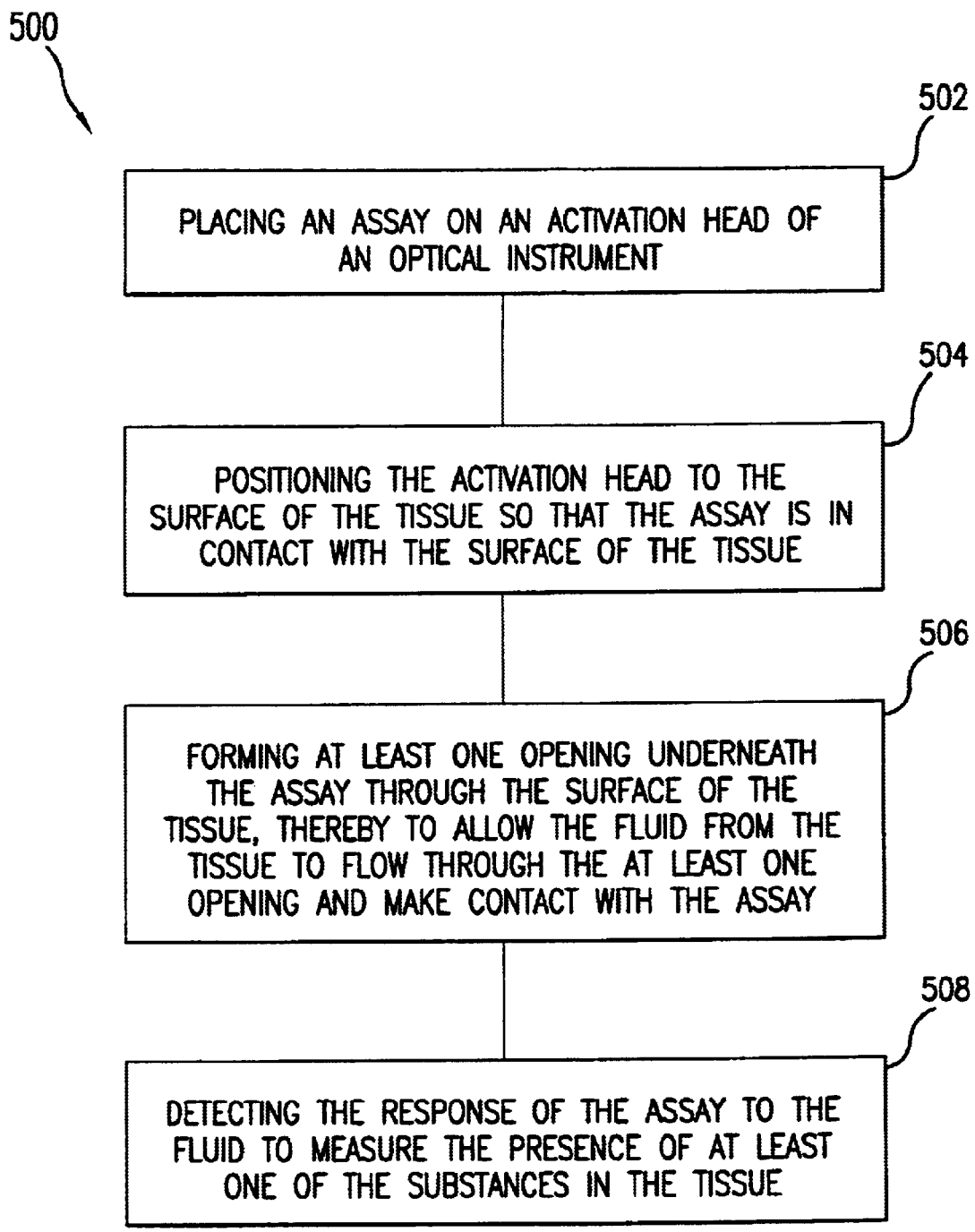
FIG. 5 is a flow chart generally depicting the overall process employing the method according to the present invention.

FIG. 5 depicts the steps involved for using system 100 to perform a measurement on tissue 40 according to the present invention. In particular, step 502 involves placing an assay device 20 on activation head 70 of optical apparatus 50. As discussed above, the assay device 20 is responsive to at least one substance in a fluid from tissue 40. One application of the present invention is where system 100 is used to measure the presence of glucose in a fluid to be collected from tissue 40; in this case the assay device 20 is responsive to glucose. The adhesive material 36 attaches the assay device 20 to the activation head 70 to maintain a proper position during the measurement.

Step 504 involves positioning the activation head 70 to the surface of the tissue 40 so that the assay device 20 is in contact with the surface of the tissue 40. It is preferable to press the activation head 70 firmly but gently against the tissue 40 so that the reactive region 24 is in direct contact with the surface of the tissue 40.

Step 506 involves forming at least one opening or micropore 41 underneath the assay 20 through the surface of the tissue 40, thereby to allow the fluid from the tissue 40 to flow through the at least one opening 41 and make contact with the assay 20 so as to wet the reactive region 24. In particular, referring to FIG. 6, step 506 involves irradiating the reactive region 24 of the base 21 with energy 39$a$, whereby the photosensitizing material in the reactive region 24 is responsive to the energy 39$a$ so as to heat up and conductively transfer heat 39$c'$ to the surface of the tissue 40 to form the at least one opening 41. Alternatively, multiple openings or micropores spaced apart from each other in the tissue may be formed. The micropore is formed through a surface of the tissue, such as skin, to a predetermined depth range into the tissue. One type of depth control of the micropore is described in more detail in commonly assigned U.S. Pat. No. 6,022,316, which is incorporated herein by reference. After the opening(s) is/are formed, the activation head 70 may be pressed against the tissue 40 to assist in drawing the fluid from the tissue 40 into the assay device 20.

Step 508 involves detecting the response of the assay device 20 to the fluid to measure the presence of the at least one of the substances in the tissue 40. Referring to FIG. 6, step 508 involves irradiating the assay device 20 with energy, such as optical energy 39$b$ or light from the second energy source 56, detecting energy 39$c$ reflected and/or scattered from the reactive region 24 of the assay device 20, and evaluating the reflected and/or scattered energy 39$c$ to determine the presence (and/or measurement) of the at least one substance in the tissue 40. The detection can be performed by an optical instrument or detecting unit 58.

Optionally, after a measurement on tissue 40 is performed, the assay device 20 can be removed from the optical apparatus 50 and disposed. Steps 502–508 as discussed above can then be repeated to perform a new measurement.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system for detecting at least one substance in a fluid to be collected from a tissue, the system comprising:

a. an assay device suitable for attachment to the tissue, wherein the assay device comprises a reactive region that is responsive to a first type of optical energy suitable to heat up and transfer heat by conduction to the tissue to ablate the tissue and form at least one opening in the tissue from which fluid is collected, and which reactive region is also responsive to at least one substance in the fluid to be collected from the tissue when the fluid is in contact with the reactive region; and b. an optical apparatus, comprising:
  an activation head;
  a first optical energy source providing as output the first type of optical energy;
  an optical detecting device that measures a characteristic of the at least one substance from the response of the reactive region when the reactive region is in contact with the at least one substance; and optical fibers for separately coupling the first optical energy source to the activation head so as to transmit the first type of optical energy from the first optical energy source outwardly from the activation head to the reactive region of the assay device to cause the formation of at least one opening in the tissue, and coupling the optical detecting device to the activation head so as to transmit optical energy indicative of the characteristic of the at least one substance from the activation head to the optical detecting device.

2. The system of claim 1, wherein the activation head of the optical apparatus is made of material suitable for absorbing heat from the tissue generated by the reactive region in response to the first type of optical energy.

3. The system of claim 1, wherein the optical apparatus further comprises a second optical energy source providing as output a second type of optical energy suitable to cause an optical interaction with the reactive region so that the optical energy scattered by and/or reflected from the assay device indicates the characteristic of the at least one substance.

4. The system of claim 3, wherein the optical apparatus further comprises a control unit that controls application of the first type of optical energy from the first optical energy source, the second type of optical energy from the second optical energy source and processing of optical energy received by the optical detecting device.

5. The system of claim 4, wherein the control unit comprises a processor for receiving and processing the optical energy to determine the characteristic of the at least one substance.

6. The system of claim 3, wherein the first optical energy source comprises a laser suitable for generating the first type of optical energy.

7. The system of claim 3, wherein the second optical energy source is an energy source selected from the group consisting of a light bulb, a tungsten halogen bulb, a noble gas filled tungsten bulb, a laser, a laser diode, or an LED.

8. The system of claim 3, wherein the optical fibers comprises at least one optical fiber for coupling the first optical energy source to the activation head, at least one optical fiber for coupling the second optical energy source to the activation head, and at least one optical fiber for coupling the optical detecting device to the activation head.

9. The system of claim 1, wherein the assay device comprises a base having a first side and a second side, and the reactive region comprises a layer of photosensitizing material disposed or deposited on the first side of the base.

10. The system of claim 9, wherein the layer of photosensitizing material is responsive to the first type of optical energy from the first optical energy source so as to heat up and conductively transfer heat to the surface of the tissue to form the at least one opening, thereby to allow fluid from the tissue to flow through the at least one opening and to make contact with the assay or to be collected.

11. The system of claim 10, wherein the layer of photosensitizing material is further responsive to the presence of the at least one substance in the fluid so that optical energy scattered by and/or reflected from the assay device includes an energy signal with a wavelength corresponding to the at least one substance.

12. The system of claim 11, wherein the layer of photosensitizing material is responsive to glucose.

13. The system of claim 9, wherein the assay device further comprises adhesive material disposed on the first side substantially surrounding the reactive region.

14. The system of claim 13, wherein the assay device further comprises adhesive material disposed on the second side of the base.

15. The system of claim 14, wherein the adhesive material on the second side of the assay device forms a mask around a window opposite the reactive region.

16. The system of claim 15, wherein the assay device is detachably attached to the activation head by the adhesive material on the second side of the base.

17. The system of claim 1, wherein the reactive region is responsive to the application of the first type of optical energy to form at least one micropore in the tissue.

18. A method for detecting a substance in a fluid from a tissue, comprising steps of:
  placing an assay device on an activation head of an optical instrument, wherein the assay device is responsive to at least one substance in the fluid;
  positioning the activation head to the surface of the tissue so that the assay device is in contact with the surface of the tissue;
  forming at least one opening underneath the assay device through the surface of the tissue, thereby to allow the fluid from the tissue to flow through the at least one opening and make contact with the assay device, the step of forming comprising irradiating photosensitizing material on the assay device with electromagnetic energy, whereby the photosensitizing material is responsive to the electromagnetic energy so as to heat up and conductively transfer heat to the surface of the tissue to form the at least one opening; and
  detecting the response of the assay device to the fluid to measure a characteristic of the at least one substance in the fluid from the tissue.

19. The method of claim 18, wherein the step of irradiating photosensitizing material comprises irradiating optical energy.

20. An apparatus for detecting substances including glucose in tissue, comprising:
  a. an activation head;
  b. a housing with an opening to receive the activation head;
  c. a first energy source located in the housing;
  d. a second energy source located in the housing;
  e. a detecting unit; and
  f. optical fibers coupling the first energy source, second energy source and detecting unit with the activation head, wherein the activation head transmits energy from the first and second energy sources, and wherein the first energy source outputs radiation through the activation head suitable to cause heating of a photosensitizing material placed in contact with a tissue to form at least one opening through the surface of the tissue issue.

21. The apparatus of claim 20, wherein the first energy source is an energy source selected from the group consisting of: a laser, a laser diode, a radio signal generator, a microwave signal generator, an acoustic signal generator, a visible signal generator, an ultraviolet signal generator, an x-ray generator, a γ-ray generator, an α-ray generator, or a β-ray generator.

22. The apparatus of claim 20, wherein the detecting unit comprises:
  a. a sensor responsive to energy reflected from and/or scattered by the photosensitizing material; and
  b. a processor coupled to the sensor for receiving and processing an output of the sensor to determine the characteristic of the at least one substance.

23. The apparatus of claim 22, wherein the processor generates a glucose measurement.

24. An assay device for detecting at least one substance in a fluid to be collected from a tissue, comprising:
   a. a base having a first side and an opposed second side; and
   b. a reactive region deposited on the first side, wherein the reactive region comprises photosensitizing material which is responsive to electromagnetic energy emitted thereon so as to heat up and conductively transfer heat to a surface of the tissue to form at least one opening, and which is responsive to at least one substance in the fluid to enable detection of a characteristic of the at least one substance in the fluid from the tissue, the reactive region comprises photosensitizing material that is reactive to glucose, the photosensitizing material comprises an enzyme system and an indicator of the at least one substance in the tissue, and wherein the photosensitizing material further comprises a derivative of phenol or aniline.

25. The assay device of claim 24, wherein the derivative includes a material selected from the group consisting of phenol, p-hydroxbenzoic acid, p-hydroxybenzene sulfonate, aniline, N-ethyl-N-(2-hydroxy-3-sulfopropyl) aniline, and N-(2-hydroxy-3-sulfoproply) aniline.

26. An assay device for detecting at least one substance in a fluid to be collected from a tissue, comprising:
   a. a base having a first side and an opposed second side;
   b. a reactive region deposited on the first side, wherein the reactive region comprises photosensitizing material which is responsive to electromagnetic energy emitted thereon so as to heat up and conductively transfer heat to a surface of the tissue to form at least one opening, and which is responsive to at least one substance in the fluid to enable detection of a characteristic of the at least one substance in the fluid from the tissue, and
   c. adhesive material disposed on the second side.

27. The assay device of claim 26, wherein the adhesive material disposed on the second side forms a mask around a window opposite the reactive region.

* * * * *